United States Patent [19]

Hofmann et al.

[11] Patent Number: 4,874,763

[45] Date of Patent: Oct. 17, 1989

[54] PHARMACEUTICALLY EFFICACIOUS PTERIDINE DERIVATIVES

[75] Inventors: Ingrid Hofmann, Frankfurt am Main; Ernst Mutschler, Mainz-Hechtsheim; Angelika Christner, Bickenbach, all of Fed. Rep. of Germany

[73] Assignee: Roehm GmbH Chemische Fabrik, Darmstadt, Fed. Rep. of Germany

[21] Appl. No.: 253,699

[22] Filed: Oct. 5, 1988

[30] Foreign Application Priority Data

Nov. 28, 1987 [DE] Fed. Rep. of Germany ....... 3740441

[51] Int. Cl.⁴ ............................................. A61K 31/50
[52] U.S. Cl. ..................................... 514/249; 544/260
[58] Field of Search ......................... 544/260; 514/249

[56] References Cited

U.S. PATENT DOCUMENTS 4,621,085 11/1986 Borchard et al. .................... 514/249

*Primary Examiner*—Mukund J. Shah
*Assistant Examiner*—C. L. Cseh
*Attorney, Agent, or Firm*—Oblon, Spivak, McClelland, Maier & Neustadt

[57] ABSTRACT

A pharmaceutically efficacious pteridine compound of formula:

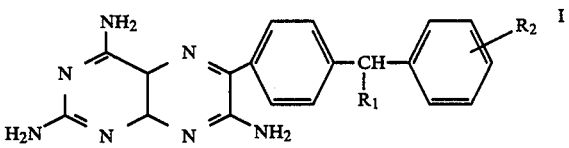

wherein $R_1$ is hydrogen, halogen, trifluoromethyl, nitro, a —$(A)_n$—$OR_3$ group, wherein $R_3$ is hydrogen or a $C_{1-6}$ alkyl group, a —$(A)_n$—$NR_4R_5$ group, wherein $R_4$ and $R_5$ independently of each other are hydrogen or a $C_{1-6}$ alkyl group or $R_4$ and $R_5$ together with the nitrogen atom form a 5- or 6-membered ring that is substituted with a $C_{1-4}$ alkyl group and wherein A is a linking group having 1 to 6 linking carbon atoms, one of which can be replaced by oxygen and wherein n is zero or one, and wherein $R_2$ is hydrogen or, independently of $R_1$, has the same meaning as $R_1$, with the proviso that $R_1$ and $R_2$ are not simultaneously hydrogen, and the physiologically acceptable acid addition salts thereof.

7 Claims, No Drawings

PHARMACEUTICALLY EFFICACIOUS PTERIDINE DERIVATIVES

BACKGROUND OF THE INVENTION

1. Field of the Invention:

The invention relates to pharmaceutically efficacious, antiarrhythmic and diuretic pteridine derivatives.

2. Description of the Background:

In 1944 Lippschitz and Hadidian (W. L. Lippschitz, Z. Hadidian, J. Pharmacol. Exp. Ther. Vol. 81, pp. 84–94 (1944); E. Mutschler & H. Knauf Publ., 30 Jahre Triamteren, Wissenschaftsverlag Köln, 1984, pp. 11–18) formulated a hypothesis about the relationship between the chemical structure and diuretic efficacy of nitrogen-containing compounds which is that the structural element

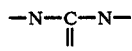

should be present in compounds as a prerequisite for diuretic activity. Even though non-supportable with facts, still this hypothesis resulted in the development of a number of diuretically efficacious structures including compounds of the purine, pyrimidine, triazine, uracil, pteridine, and other heterocycle classes. Of particular note is 2,4,7-triamino-6-phenylpteridine (U.S. Pat. No. 3,081,230), which has proven to be an excellent potassium sparing drug (Triamterene). Weinstock & Wiebelhaus have researched the relationship between chemical structure and diuretic action of approximately 500 pteridine derivatives (cf. K. Fellinger, Therapie mit Triamteren, Georg Thieme Verlag 1967, pp. 2–21). However, the correlations which have been made have not remained unrefuted. (Cf. E. Wolf in E. Mutschler & H. Knauf, 30 Jahre Triamteren, loc., cit., pp. 11–18). Thus, G. H. Mudge finds in Goodman-Gilman "The Pharmacological Basis of Therapeutics," 5th Ed., McMillan Publishing Co., Inc., p. 838, with respect to Triamterene: "It is a pteridine compound, related chemically to folic acid. The diuretic activity of closely related homologues of Triamterene has been examined, but no specific structural requirements have been established."

At variance with the hypothesis developed by Weinstock & Wiebelhaus, it has been found that derivatives of Triamterene, in which the para-position of the 6-phenyl ring is etherified with a hydrophilic group, have a diuretic and anti-potassium uretic activity (GB Pat. No. 1,597,881; DE-A 34 07 695). U.S. Pat. No. 4,621,085 (or DE-A 34 12 765) shows cardioactive, in particular, antiarrhythmic properties for pharmaceutical drugs which contain Triamterene derivatives as the active substance, whose 6 phenyl group is substituted lipophilically in the paraposition. Fluorine, chlorine branched or cyclic alkyl having 3 to 6 carbon atoms, benzyl, trifluoromethyl or nitro-substituents in particular are suitable lipophilic substituents.

The previous ideas concerning the correlation between structure and action are seriously questioned by the Triamterene derivatives which have more recently been discovered and reported in the patent literature. Apparently the relationships contributing to the desired pharmaceutical properties are quite complex so that the relevant finding in the DE-A 34 07 697 is still valid; "A number of parameters go into the profile of an active substance such as efficacy, acute and chronic toxicity, compatibility with other active substances, pharmacokinetics and dynamics, metabolism, physical and chemical parameters such as stability, solubility, accessibility, and the like. However, the state of the art is such that it does not offer any criteria regarding what direction to look for further development of existing structures in order to achieve improved properties. In particular, there is a need for compounds that can be administered orally, whereby, however, no fewer demands were to be made on the other pharmacological properties than those of prior art. It was found surprisingly that derivatives of para-benzyltriamterene come very close to these requirements or even surpass them.

A need therefore continues to exist for pharmaceutically efficacious compounds which exhibit antiarrhythmic and diuretic properties.

SUMMARY OF THE INVENTION

Briefly, these objects and other objects of the present invention as hereinafter will become more readily apparent can be attained by a pteridine compound of the formula:

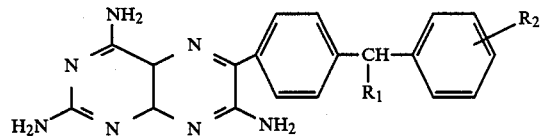

wherein $R_1$ is hydrogen, halogen, trifluoromethyl, nitro, a —$(A)_n$—$OR_3$ group, wherein $R_3$ is hydrogen or $C_{1-6}$ alkyl having preferably 1 to 3, in particular 1 to 2 carbon atoms, or a —$(A)_n$—$NR_4R_5$ group, wherein $R_4$ and $R_5$ each is independently hydrogen or a $C_{1-6}$ alkyl group, having preferably 1 to 2 carbon atoms, or $R_4$ and $R_5$ together form, with the nitrogen atom and, if desired, including another nitrogen or oxygen atom, a 5- or 6-membered ring, which optionally is substituted with a $C_{1-2}$ alkyl groups, A is a bridging group, preferably a $C_{1-6}$ alkylene chain and n is zero or one, and wherein $R_2$ is hydrogen or has the same meanings as $R_1$, subject to the conditions that $R_1$ and $R_2$ do not simultaneously denote hydrogen. The present invention also includes physiologically acceptable acid addition salts of the compound.

DETAILED DESCRIPTION OF THE PREFERRED EMBODIMENTS

Preferably, either the $R_1$ or $R_2$ group in the present compound is hydrogen. Preferred compounds also include those wherein $R_1$ or $R_2$ is a halogen having an atomic weight ranging from 19 to 80. Preferred compounds also include those wherein $R_1$ is —OH.

Provided $R_2$ is not hydrogen, this substituent is preferably in para-position to the benzylic carbon atom. Preferred substituents in the para-position of the para-benzyltriamterene are fluoro-, chloro-, bromo-, trifluoromethyl-, hydroxy-, if desired, substituted amino- and nitro groups. Furthermore, preferred embodiments of the compound of the invention are those which have non-substituted phenyl groups or hydroxy substituted phenyl and those where $R_1$ is amino- or nitro. The —$NR_4R_5$ group together with another nitrogen or if desired, oxygen atom form a 5- or 6-member ring. The ring can be substituted with a $C_1$–$C_2$ alkyl group. Suitable ring systems include morpholinyl, piperidinyl, pyrrolidinyl and the like. Preferred is alkyl, more preferably $C_{1-4}$-alkyl substituted piperazinyl.

The compounds of formula I have a chiral center. The present invention encompasses all forms that can be distinguished with respect to the chirality. The compounds are generally yellowish, crystalline, and have a high-melting point. The compounds of formula I show the strong fluorescene in ultraviolet light that is a property of the pteridine compounds. This property can be used for detection of the compounds. Compounds of formula I include the following:

2,4,7-triamino-6-[4-(4'-chlorobenzyl)-phenyl]-pteridine, (p-chlorobenzyl-triamterene)

2,4,7-triamino-6-[4-(4'-fluorobenzyl)-phenyl]-pteridine, (p-fluorobenzyl-triamterene)

2,4,7-triamino-6-[4-(4'-bromobenzyl)-phenyl]-pteridine, (p-bromobenzyl-triamterene)

2,4,7-triamino-6-[4-(4'-trifluoroemethylbenzyl)-phenyl]-pteridine, (p-trifluoromethyl-benzyltriamterene)

2,4,7-triamino-6-[4-(4'-hydroxybenzyl)-phenyl]-pteridine, p-hydroxybenzyl-triamterene)

2,4,7-triamino-6-[4-(4'-nitrobenzyl)-phenyl]-pteridine, (p-nitrobenzyl-triamterene)

2,4,7-triamino-6-[4-(4'-aminobenzyl)-phenyl]-pteridine, (p-aminobenzyl-triamterene).

2,4,7-triamino-6-[4-($\alpha$-N,N-dimethylaminobenzyl)-phenyl]pteridine 2,4,7-triamino-6-[4-($\alpha$-morpholinobenzyl)-phenyl]-pteridine 2,4,7-triamino-6-[4-($\alpha$-N-methylpiperazino)benzyl)-phenyl]-pteridine A preferred compound is (Phenyl-)[4-(2,4,7-triamino-pteridinyl-6)-phenyl]-methanol [p-($\alpha$-hydroxyenzyl)-triamterene] and the p-nitrophenyl-, p-chlorophenyl, p-fluorophenyl-, p-bromophenyl, p-hydroxyphenyl-, p-aminophenyl-, p-dimethylaminophenyl derivatives thereof and the ethers thereof, in particular the methyl- and the ethyl ether. Another compound is $\alpha$-(4-(2,4,7-triamino-pteridinyl-16)phenyl]benzyl-dimethylamine (p-benzyl-dimethylaminotriamterene) and derivatives thereof substituted with fluoro-, chloro-, bromo-, amino-, nitro-, and hydroxy groups on the benzyl group, in particular at the paraposition. Still another preferred compound is (phenyl)[4-(2,4,7-triamino-pteridinyl-6)-phenyl]-nitromethane and its derivatives, substituted by fluoro-, chloro, bromo-, amino-, nitro- or hydroxy groups on the phenyl group, in particular in the para-position.

The compounds of formula I can be prepared by the following scheme although this method of synthesis is not meant to be exclusive. In principle the end products of formula I can be prepared by the triamterene synthesis of R. G. W. Spickett & G. M. Timmis as described in J. Chem. Soc. 2887 (1954) by ring closure reaction of a substituted benzyl cyanide having the formula II:

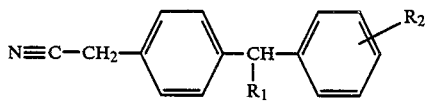

wherein $R_1$ and $R_2$ have the above described meanings, with 2,4,6-triamino-5-nitrosopyrimidine of formula III:

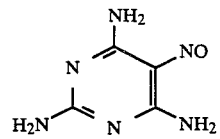

under conditions that are suitable for condensation. These conditions include the ring forming condensation reaction of compound II and III under base catalysis in a suitable solvent, for example an alcohol. Suitable alcohols in particular include ether alcohols such as 1-methoxy-2-propanol. Suitable bases include the alkali alcoholates produced by dissolving an alkali metal, in particular sodium, in the alcohol. Normally, it is expedient to employ an amount of the compound of formula II in a specific negligible excess with respect to the compound of formula III. Preferably, the conversion is conducted while heating, for example, at about 70°–120° C., advantageously up to the boiling point of the alcohol, i.e., under reflux. Generally, a reaction period of several hours suffices with a usual reaction period of about 2 hours. For work-up it is expedient to cool the reaction mixture to room temperature and then precipitation is triggered by the addition of a solvent, said precipitation can be completed by letting the mixture stand for example at temperatures below room temperature.

The compound of formula I can be purified in the conventional manner, for example, by converting it into an acid addition salt, for example, with aqueous acetic acid, then dissolving the salt in a boiling solvent, if necessary, while adding activated carbon thereto, and then cooling the solution to crystallize the salt.

The compound of formula I can be liberated from the acid addition compound through treatment with a suitable, preferably aqueous base, e.g., by means of concentrated ammonia water.

The yields vary. However, they can be as high as greater than 90% of the theoretical yield.

As a rule the compounds of formula I yield crystalline products. Their purity can be checked, for example, with the acid of thin-layer chromatography.

NMR data and ultimate analysis confirm the aforementioned structures.

The starting material of formula II in its various embodiments can be prepared in the conventional manner or by other existing methods.

A suitable key intermediate can be, for example, a compound having the formula IV:

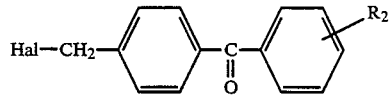

wherein Hal stands for halogen, preferably bromine and $R_2$ has the aforementioned meanings, whereby instead of Hal groups, cyano groups can be introduced through conversion with an alkali cyanide, for example, in alcohol as a solvent.

Compounds of formula II, wherein $R_1$ stands for —OH, can be obtained for example through reduction of the carbonyl group by means of sodium boro hydride in an (aqueous) ether such as dioxane. The OH functional group can serve as the basis for conversion into other functional groups, included in the meaning of $R_1$, for example, by conversion into a leaving group such as the tosyl group which it then converted into an amino group by reaction with the amine $HNR_4R_5$. A reactive intermediate can also be produced, for example, through bromination of a cyanomethyl-diphenylmethane that is substituted, if necessary, with N-bromosuccinimide, i.e., the compound of formula II, wherein $R_1$ stands for bromine.

Compounds of formula II are also accessible in part via the nitrodiphenylmethane having the formula V:

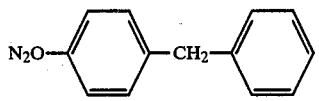

The nitrodiphenylmethane compound V can be obtained through Friedel-Craft synthesis starting with a nitrobenzyl chloride. Thus, the use of benzene, which imposes a risk to health, can be avoided. The compound of formula V can also be prepared for example through reduction of 4-nitrobenzophenone by means of a suitable reducing agent such as triethylsilane, for example, in dichloromethane.

The compound having the formula VI:

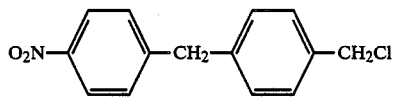

or its positional isomers, which can be converted to the nitrile IIA, wherein $R_1=H$ and $R_2=$nitro, with alkali cyanide, can be prepared in the conventional manner from the compound of formula V or a positional isomer thereof through chloromethylation, e.g., by means of zinc chloride/trioxane. The compound IIA in turn is the starting point for reduction of the nitro group to the amino function, for example, with zinc and alcoholic hydrochloric acid, whereby the compound IIB ($R_1=H_1$, $R_2=NH_2$) is formed. The diazotization of compound IIB opens the possibility of introducing other groups, which fall under the meaning of $R_2$. For example, diazotization followed by refluxing in an aqueous medium results in the introduction of phenolic OH groups. (Compound IIC; $R_1=H$; $R_2=OH$). The prestages of preparation are well-known or can be prepared in accordance with or with reference to the existing processes.

APPLICATION OF COMPOUNDS OF FORMULA I

The compounds of formula I are lipophilic, which is influenced by the type and the position of the $R_2$ substituent and by the type of $R_1$ substituent. For example, the compounds of formula I, wherein $R_1$ stands for hydrogen and $R_2$ stands for fluorine, chlorine, bromine, or —$CF_3$, may be regarded as very lipophilic. Generally the solubility of these lipophilic representatives in the isotonic phosphate buffer pH 7.4 is at less than 2 mg/l.

The compounds of the invention have anti-arrhythmic and diuretic properties. In particular they possess anti-potassium uretic efficacy.

The anti-arrhythmic activity of a substance can be determined, for example, by model research. One suitable test method is, that of V. Borchard, R. Böskep and K. Greeff, Arch. intern. Pharmacodyn. Therap. 256 (2) 253 (1982). In this method, arrhythmia or asystole is induced by means of a 50 Hz alternating current at the isolated left vestibulum and at the right, ventricular papillary muscle of the guinea pig.

Pharmaceutical preparations, containing the active substance of formula I, can be prepared in the conventional manner. The formulations can contain the usual carrier and auxiliary substances. One embodiment of the invention represents solid preparations that are suitable for oral administration such as pills, capsules, tablets, and the like. For oral application suitable carrier materials include pharmaceutically indifferent solids such as mannitol, lactose, organic or inorganic calcium salts, and the like. Suitable binders include, among others, polyvinyl pyrrolidone, gelatines and cellulose derivatives. Agents which expand such tablets as starch or alginic acid, lubricants such as stearic acid or its salts and inorganic mobile agents such as talcum or colloidal silicic acid and taste modifiers can also be used as additives.

The active substances can be mixed with the auxiliary agents in the conventional manner and granulated in the wet or dry state. Depending on the type of the additives used, a powder that can be directly made into tablets can also be obtained, if necessary, by simply blending. The granules or powder can be filled directly into capsules or moulded in the conventional manner into tablet cores.

In the case of parenteral administration the therapeutic drugs can also be prepared and administered in the conventional manner.

Having now generally described this invention, a further understanding can be obtained by reference to certain specific examples which are provided herein for purposes of illustration only and are not intended to be limiting unless otherwise specified.

EXAMPLES

A. The following is an example of a tableted pharmaceutical preparation.

A mixture comprising

| active substance of formula 1 | 16.67 kg |
|---|---|
| lactose | 54.32 kg |
| cellulose powder | 15.00 kg |
| talcum | 5.08 kg |
| corn starch | 2.91 kg |
| calcium carbonate | 2.50 kg |
| calcium carboxymethyl cellulose | 1.81 kg |
| magnesium stearate | 0.74 kg |
| polyvinyl pyrrolidone (25000) | 0.52 kg |
| highly dispersive silicium dioxide | 0.45 kg | is molded into tablet cores.

B. The following examples serve to explain the manufacture of compounds: Intermediates are identified by means of gas chromatography/mass spectroscopy. The compounds of formula I of the invention are identified by NMR and ultimate analysis.

1. PREPARATION OF COMPOUNDS OF FORMULA I 1.1

2,4,7-Triamino-6[4(4'-fluorobenzyl)phenyl]-pteridine

Feedstock:

| 164.5: mmole 4-fluorobenzyl-benzylcyanide | 37.0 g |
|---|---|
| 149.3 mmol 2,4,6-triamino-5-nitrosopyrimidine (TNP) | 23.0 g |

-continued

| | |
|---|---|
| 151.0 mmole sodium | 3.5 g |
| 900.0 ml 1-methoxy-2-propanol | |

In a 2 liter round bottom flask 3.5 g of sodium are dissolved in 500 ml of 1-methoxy-2-propanol. To this 23.0 g of TNP, 37.0 g of 4-fluorobenzyl-benzylcyanide and 400 ml of 1 methoxy-2-propanol are added. The reaction mixture is refluxed for 2 hours. The precipitate formed after 72 hours at +4° C. is siphoned off via a D4 glass suction funnel and is washed with 250 ml of 1-methoxy-2-propanol and 500 ml of acetone. The raw product is dried for 18 hours at 60° C. in a vacuum drying oven (oil pump) and subsequently recrystallized from 6 liters of 30% acetic acid and 10 g of activated carbon. The activated carbon is removed, using a plaited filter and membrane filter (0.2 µ). The precipitate formed at 25° C. is siphoned off via a D4 glass suction funnel and suspended in 1 liter of $H_2O$. The suspension is set at a pH of 10.0 with a concentrated $NH_3$ solution and stirred at 25° C. for 18 hours. The precipitate is siphoned off via a D4 glass suction funnel, washed to neutral with $H_2O$, and washed with 800 ml of acetone. The product is dried in a vacuum oven (oil pump) at 60° C. for 18 hours and at 105° C. for 5 hours.

Yield: 19.8 g=36.7% total product yield.

| $C_{20}H_{16}N_7F_3$ MW 411.39 | | | |
|---|---|---|---|
| C | H | N | F |
| calculated | 63.2% | 4.5% | 27.1% | 5.3% |
| found | 63.1% | 4.5% | 27.0% | 5.3% |

Solubility in isotonic phosphate buffer pH 7.4 <2 mg/l buffer

1.2
2,4,7-Triamino-6[4(4'-chlorobenzyl)phenyl]pteridine

Feedstock:

| | | |
|---|---|---|
| 5.5 g | = 22.75 mmole | 4-chlorobenzyl-benzylcyanide |
| 3.14 g | = 20.5 mmole | 2,4,6-triamino-5-nitrosopyrimidine (TNP) |
| 0.48 g | = 20.9 mmole | sodium |
| 127.0 ml | | 1-methoxy-2-propanol |

In a 250 ml round-bottom three-necked flask equipped with calcium chloride drying tube, condenser, and magnetic stirrer, 0.48 g of sodium were dissolved in 100 ml of 1-methoxy-2-propanol. After the sodium had been completely dissolved, 3.14 g of TNP and 5.5 g of 4-chlorobenzyl-benzylcyanide of the alcoholate solution were added. Residues of the substances were rinsed with 27 ml of 1-methoxy-2-propanol and the feedstock was boiled under reflux for 2 hours. After the feedstock was cooled to room temperature, the yellow precipitate formed during the reaction was siphoned off via a D-4 frit, rewashed with a little 1-methoxy-2-propanol and diethyl ether. The raw product was dried for 16 hours at 60° C. in a vacuum drying oven (oil pump).

Yield: 6.0=77.5% of the theoretical yield (raw product).

$C_{19}H_{16}N_7Cl$ MW=377.87.

1.3
2,4,7-Triamino-6[4(4'-bromobenzyl)phenyl]pteridine (=p-bromobenzyl-triamterene)

The above product compound is prepared in the same manner as described in 1.2 from 3.5 g of p-bromobenzyl-benzylcyanide.

Yield: 3.9 g=86.3% of the theoretical yield (raw product).

$C_{19}H_{16}N_7Br$ MW=422.30.

1.3.1 Purification of p-chlorobenzyl- o p-bromobenzyl-triamterene

A 6.0 g amount of p-chlorobenzyl-triamterene is dissolved in 1.2 liters of refluxing 30% acetic acid. The clear, yellow solution is added to 2.0 g of activated carbon and the activated carbon is removed by filtration via a plaited filter and membrance filter (0.2 µ, glass fiber roughing filter). After cooling the solution to room temperature, at which time a yellow precipitate forms, the suspension is stored in a refrigerator for 16 hours for complete recrystallization. The precipitated p-chlorobenzyl triamterene is siphoned off via a D-4 frit and suspended in 100 ml of water. With 125 ml of 1M and 25 ml of 25% ammonia water, the mixture is raised to a pH of 10 and stirred at room temperature for 3 hours. After checking the pH value (pH 10), the precipitate is siphoned off, washed with 100 ml of water and then dried in a vacuum drying oven (oil pump) at 60° C. for 16 hours. After milling, the precipitate is dried once again in the vacuum drying oven at 105° C. for 5 hours.

Yield: 4.8 g=80.0% of the theoretical yield.

The 3.9 g of p-bromobenzyl-triamterene are recrystallized analogously from 780 ml of 30% acetic acid, using 1.3 g of activated carbon, and the base is liberated from the acetate with 80 ml of 1M and 16 ml of 25% ammonia water (up to pH 10).

Yield: 3.1 g of 79.5% of the theoretical yield.

1.4.
2,4,7-Triamino-6-[4-(4'-trifluorobenzyl)phenyl]pteridine (=p-trifluoromethyl-benzyl-triamterene)

Feedstock:

| | |
|---|---|
| 11.4 mmole sodium | 0.26 g |
| 11.0 mmole 2,4,6-triamino-5-nitrosopyrimidine | 169 g |
| 12.2 mmole 4-(4'-cyanomethylbenzyl)benzotrifluoride | 3.38 g |
| 68.0 ml 1-methoxy-2-propanol abs. | |

Procedure:

In a 250 ml round-bottom three-necked flask, 0.26 g of sodium are dissolved in 50 ml of 1-methoxy-2-propanol. To this solution, 1.69 g of TNP and 3.38 g of 4-(4'-cyanomethylbenzyl)benzotrifluoride are added, which is rinsed completely with 18 ml of solvent. The reaction mixture is heated to boiling and refluxed for 2 hours. As the feedstock is cooled to room temperature, a yellow precipitate is formed. This is siphoned off via a D-4 glass suction funnel and washed with 10 ml of ice-cold solvent, 25 ml of acetone, and 50 ml diethyl ether. The filtrate residue is dried for 18 hours at 60° C. in a vacuum drying oven (oil pump). The entire raw yield (2.8 g) is dissolved in 840 ml of refluxing 30% acetic acid, stirred and refluxed further for a short period of time with 0.9 g of activated carbon. To remove the activated carbon, the mixture is filtered via a plaited filter and then via a membrane filter (0.2 µ with glass-fiber roughing filter). The totally transparent filtrate is slowly cooled to room temperature, whereby the substance precipitates. The triamterene derivative which has crystallized is removed via a D-4 glass suction funnel and washed with about 200 ml of water.

1.5.
2,4,7-Triamino-6-[4-(2-hydroxybenzyl)phenyl]pteridine

Feedstock:

| 1.70 g | = 7.6 mmole | 4-cyanomethyl-2'-hydroxy-diphenylmethane |
| --- | --- | --- |
| 0.34 g | = 14.7 mmole | sodium |
| 1.03 g | = 6.8 mmole | 2,4,6-triamino-5-nitrosopyrimidine (TNP) |
| 42.0 ml | = | 1-methoxy-2-propanol |

Procedure

A 0.34 g amount of sodium is dissolved in 30 ml of 1-methoxy-2-propanol. After the sodium has been completely dissolved, 1.7 g of 4-cyanomethyl-2'-hydroxy-diphenylmethane and 1.03 g of TNP are added. Residues of the substance are rinsed with 12 ml of 1-methoxy-2-propanol. The mixture is boiled under reflux for 2 hours. The result is a transparent, dark-brown solution. Then the mixture is cooled to room temperature and 140 ml of acetone are added, whereby the sodium salt of the phenolate forms as a precipitate. The mixture is stored in the refrigerator for 20 hours for complete recrystallization. Then the precipitate is siphoned off via a D-4 frit and rewashed with acetone. The triamterene derivative is dried in a vacuum drying oven at 60° C. for 2 hours.

Yield: 2.7 g=104% of the theoretical yield (based on sodium salt).

1.6
2,4,7-Triamino-6-[4-hydroxybenzyl)phenyl]pteridine

In an analogous manner 1.0 g=86.4% of the theoretical yield of the sodium salt of the corresponding triamterene derivative is prepared from 0.8 g=3.6 mmole 4-cyanomethyl-4'-hydroxyldiphenylmethane.

Purification of 2,4,7-Triamino-6-[4-(2-hydroxybenzyl)phenyl]pteridine

A 2.7 g amount of TBzl-O-Na salts is dissolved in 250 ml of boiling 20% acetic acid. The solution is boiled under reflux with 0.45 g of activated carbon for 5 minutes. Then the activated carbon is removed by filtration via a plaited filter and the filtrate is membrane-filtered (0.2 μ, glass fiber roughing filter). The solution cools to room temperature, whereby the product precipitates out again. For complete crystallization, the suspension is stored in a refrigerator for 72 hours. The precipitate is siphoned off via a D-4 frit, rewashed with little water and acetone and dried in a vacuum drying oven at 60° C. for more than 16 hours. Then the triamterene derivative is dried in a vacuum drying oven at 105° C. for 5 hours.

Yield: 1.7 g=59.6% of the theoretical yield (calculated as monoacetate).

A 1.0 g amount of 2,4,7-triamino-6-[4-(4'-hydroxybenzyl)phenyl]-pteridine-Na salt was recrystallized in an analogous manner.

Yield: 600 mg=56.8% of the theoretical yield (calculated as monoacetate).

1.7.
2,4,7-Triamino-6-[4-(α-hydroxybenzyl)-phenyl]pteridine

Feedstock:

| 4.4 | g = 19.7 mmole | 4-cyanomethyl-diphenylcarbinol |
| --- | --- | --- |
| 2.7 | g = 17.3 mmole | 2,4,6-triamino-5-nitrosopyridimidine |
| 438.0 | g = 18.7 mmole | sodium |
| 106.9 | ml = | 1-methoxy-2-propanol |

Procedure

The process is conducted in an analogous manner as in the preparation of 1.5, whereby the product formed as a precipitate by means of 900 ml diethyl ether.

Yield: 5.4 g=86.9% of the theoretical yield.

A 5.4 g amount of the product thus obtained is purified by recrystallization from 540 ml of 20% acetic acid, using 1.7 g of activated carbon. The end product is liberated from the acetate with 1M of ammonia water, siphoned off, rewashed with a little water, dried first of all in a vacuum drying oven at 60° C. for 18 hours, and then at 105° C. for 5 hours.

Yield: 2.8 g=51.9% of the theoretical yield.

1.8.
2,4,7-Triamino-6[4(α-N,N-dimethylaminobenzyl)-phenyl]pteridine

Feedstock:

| 2.8 g = | 11.2 mmole 4-cyanomethyl-diphenylmethyl-dimethylamin |
| --- | --- |
| 1.67 g = | 9.8 mmole 2,4,6-triamino-5-nitrosopyrimidine |
| 248.9 mg = | 10.6 mmole sodium |
| 59.9 ml | 1-methoxy-2-propanol |

In a 100 ml round bottom three neck flask equipped with a condenser, drying tube and magnetic stirrer and an oil bath 248.9 mg of sodium are dissolved in 40 ml of 1-methoxy-2-propanol. When the sodium is completely dissolved 2.8 of 4-cyanomethyl diphenylmethyl dimethylamine and 1.67 TNP are added. Residues of substances are rinsed with additional 1-methoxy-2-propanol. The reaction mixture is heated to boiling and refluxed for 2 hours. After cooling to room temperature a yellow precipitate is formed, which is filtered off. After washing with acetone and diethylether the solid material is dried for 6 hours at 60° C. in a vacuum drying oven (oil pump).

Yield: 3.1 g=81.9% of the theoretical yield.

1.9.
2,4,7-Triamino-6[4(-α-morpholinobenzyl)-phenyl]pteridine

In an analogous manner as described for 1.8 the title compound is prepared:

| 2.35 g | = 8.01 mmole 4-cyanomethyl-diphenylmethyl-morpholin |
| --- | --- |
| 1.24 g | = 7.28 mmole 2,4,6-triamino-5-nitrosopyrimidine |
| 172.1 mg | = 7.35 mmole sodium |
| 45.0 ml | 1-methoxy-2-propanol |

Yield: 2.3 g=73.7% of the theoretical yield.

1.10. 2,4,7-Triamino-6[4(-α-(N-methylpiperazino)benzyl)-phenyl]pteridine

In an analogous manner as described for 1.8 the title compound is prepared.

Feedstock:

| | |
|---|---|
| 5.0 g = 18.3 mmole | 4-cyanomethyl-α-(N—methylpiperazino)-diphenylmethane |
| 2.3 g = 14.8 mmole | 2,4,6-triamino-5-nitrosopyrimidine |
| 353.0 mg = 15.0 mmole | sodium |
| 91.5 ml | 1-methoxy-2-propanol |

Yield: 4.4 g≙67.3% of the theoretical yield.

1.10.1 Purification of 2,4,7-Triamino-6[4(α-N,N-dimethylaminobenzyl)-phenyl]pteridine, 2,4,7-Triamino-6[4(α-morpholinobenzyl)phenyl]pteridine and 2,4,7-Triamino-6[4(α(N-methylpiperazino)benzyl)-phenyl]pteridine.

Procedure:

3.1 g of 2,4,7-triamino-6-[4-(α-N,N-dimethylamino-benzyl-)phenyl-]pteridine (1.8) are dissolved in a mixture of 126 ml of ethanol plus 1 molar hydrochloric acid with boiling. The solution is treated with 1 g of activated charcoal. The charcoal is filtered off by means of a plaited filter and a membrane filter (0.2 μ glass fiber prefilter) by which traces of charcoal are removed. On cooling to room temperature a precipitate is formed. The suspension is kept in a refrigerator for 16 hours. The precipitate is then filtered off and is suspended in 100 ml of water. The mixture is adjusted to pH 10, is stirred at room temperature over night and after controlling pH the precipitate is obtained by filtration. It is washed with water and is subsequently dried at 60° C. for 16 hours in a vacuum drying oven.

Yield: 2.4 g≙77.4% of the theoretical yield.

Solubility (in isotonic phosphate buffer at pH 7.4) 0.63 mg/l melting point (decomposition): 288° C. 4.4 g of 2,4,7-triamino-6-[4(-α-morpholinobenzyl)-phenyl]-triamterene are recrystallized from 84.6 ml of 1-methoxy-2-propanol using 1.0 g of activated charcoal as described above. The suspension which is obtained on cooling is stored in a refrigerator for 16 hours. The precipitate thus formed is filtered off, is then resuspended in 200 ml of diethyl ether and is stirred for 20 hours at room temperature. The precipitate is again filtered off, is washed with diethyl ether and is dried in a vacuum drying oven at 105° C. for 20 hours.

Yield: 1.83 g≙28.0% of the theoretical yield solubility (in isotonic phosphate buffer pH 7.4)=130 mg/l, melting point: 250° C.

2.3 g of 2,4,7-triamino-6[4-(α-(N-methylpiperazino)-benzyl)phenyl]pteridine are recrystallized from 104 ml of 1 molar hydrochloric acid as described above. After recrystallization the pH is adjusted to 10.0.

After 16 hours stirring the compound is filtered off and dried.

Yield: 1.3 g≙41.6 g of the theoretical yield solubility (in isotonic phosphate buffer solution pH 7.4)=20.0 mg/l melting point: 250° C.

Other compounds of formula I can be prepared analogously to the above procedure.

2. PREPARATION OF COMPOUNDS OF FORMULA II:

2.1 4-Fluorobenzyl-benzylcyanide

Feedstock:

| | |
|---|---|
| 193.9 mmole 4-chloromethylphenyl-4'-fluorophenylmethane | 45.5 g |
| 251.1 mmole sodium cyanide (NaCN) | 12.3 g |
| water | 12.0 ml |
| ethanol | 42.6 ml |

Procedure:

In a 250 ml round-bottom flask, 12.3 g NaCN and 12 ml H₂O are added and heated to 80° C. After 20 minutes, a solution of 45.5 g of chloromethylphenyl-fluorophenylmethane is added dropwise into 42.6 ml of ethanol within 20 minutes. The reaction mixture is boiled under reflux for 5 hours. The precipitate formed at room temperature is siphoned off via a D-4 glass suction funnel and washed with 80 ml of ethanol. The entire filtrate is concentrated in a rotary evaporator. The residue is absorbed in 200 ml of diethyl ether and washed to neutrality four times with 130 ml of H₂O each time. The organic phase is dried with Na₂SO₄ and concentrated in a rotary evaporator. The raw product (42.3 g) is filtered over silica gel (1000 g) with diethyl ether (1:4).

Yield: 37.0 g=84.7% of the theoretical yield of the feedstock.

2.2 4-Chloro- or 4-bromobenzyl-benzylcyanide

Feedstock:

| | | |
|---|---|---|
| 13.0 g = | 51.8 mmole | 4-chloro-4'-chloromethyldi-phenylmethane |
| 3.3 g = | 67.3 mmole | sodium cyanide |
| 3.2 ml | water | |
| 11.4 ml | ethanol, 96% | |

Procedure:

In a 50 ml round-bottom three-necked flask, 3.3 g of sodium cyanide are dissolved in 3.2 ml of water at 80° C. The 13 g of 4-chloro-4'-chloromethyldiphenylmethane, dissolved in 11.4 ml of ethanol, are added dropwise into the NaCN solution within 30 minutes. The reaction mixture is boiled under reflux for 5 hours. The mixture turns dark-brown and a fine crystalline precipitate is formed. After the reaction mixture has cooled to room temperature, the sodium chloride is siphoned off via a D-4 glass suction funnel, the precipitate is rewashed with 15 ml ethanol, and the concentrated organic phases are concentrated in a rotary evaporator (bath temp. 40° C., water-jet vacuum). The residue is absorbed in 100 ml of diethyl ether and washed three times with 50 ml of H₂O each time. The ether phase is dried over sodium sulfate and after removing the drying agent by filtration, concentrated in a rotary evaporator (bath temp. 40° C., water-jet vacuum). The residue (10 g) is recrystallized in 50 ml of n-pentane and 30 ml of diethyl ether. The crystalline precipitate precipitates at room temperature. For complete crystallization, the feedstock is stored in a refrigerator overnight. The resulting precipitate is siphoned off, rewashed with little ice-cold n-pentane, and dried in a vacuum drying oven (oil pump) at room temperature for 2 hours.

Yield: 5.5 g of 43.9% of the theoretical yield.

10.1 g of 98.6% of the theoretical yield 4-bromobenzyl-benzylcyanide (raw product) is prepared in an analogous manner from 11.1 g of 4-bromo-4'-chloromethyldiphenylmethane and recrystallized from 60 ml of diethyl ether and n-pentane (1:1).

Yield: 3.6 g=33.5% of the theoretical yield.

2,3. 4-(4'-Cyanomethylbenzyl)benzotrifluoride

Feedstock:

| 32.3 mmole | 4-(4'-chloromethylbenzyl)benzotrifluoride | 9.2 g |
| 42.0 mmole | sodium cyanide water | |

Procedure:

In a 50 ml round-bottom two-necked flask, 2.0 g were suspended in 2.0 ml of water and heated to 80° C. A 9.2 g amount of 4-(4'-chloromethylbenzyl)benzotrifluoride was dissolved in 7.1 ml of ethanol. This solution was added dropwise into the NaCN suspension. The proportion of undissolved substances increased. The reaction mixture turned brown. The feedstock was boiled under reflux for 5 hours. After the reaction mixture had cooled down to room temperature, the solid substance was removed by filtration and washed with 30 ml ethanol. The filtration was concentrated in a rotary evaporator (bath temp. 30° C., water-jet vacuum). The oily residue was dissolved in 50 ml of diethyl ether and washed to neutrality four times with 30 ml of water each time. The organic phase was dried over sodium sulfate. The drying agent was removed by filtration and the ether was removed by distillation in a rotary evaporator (bath temp. 30° C., water-jet vacuum). The raw product (8.0 g) was chromatographed on silica gel 60 (0.63–0.200) with ether/pentane ($\frac{1}{4}$) and the 4-(4'-cyanomethylbenzyl)benzotrifluoride (5.8 g) thus obtained was recrystallized from 44 ml of solvent blend (petroleum benzin 60°–80°C0-diethyl ether 5:1 v/v). The precipitated crystallizate was removed by filtration via a D-4 glass suction funnel and washed with 25 ml of ice-cold petroleum benzin. The product was dried in a vacuum drying oven (oil pump) at room temperature for 5 hours.

Yield: 3.39 g=38.1% of the theoretical yield.

2.4 2-Hydroxybenzylbenzylcyanide

Feedstock:

| 10.0 g = | 4.5 mmole | 2-aminobenzyl-benzylcyanide |
| 19.7 ml | | water |
| 8.3 ml | | sulfuric acid, 25% |
| 300.0 mg | | sodium nitrite |

Procedure:

Into a 100 ml round-bottom three-necked flask with condenser and drop funnel, as well as oil bath and magnetic stirrer, 1.0 g of 25% 2-aminobenzyl-benzylcyanide, 15.8 ml of water, and 8.3 ml of sulfuric acid, are placed and the mixture is heated to boiling. A solution of 300 mg of sodium nitrite is added dropwise to this mixture in 3.9 ml of water within 1 hour. The mixture is boiled under reflux for 10 minutes and then the mixture is cooled down to room temperature. The mixture is extracted with 100 ml of diethyl ether; the organic phase is dried over sodium sulfate and upon removing the drying agent by filtration, the ether is siphoned off by a rotary evaporator. Since a part of the substances resinifies as the product increases, another 3 g of educt is converted in this amount of product.

Total yield: 3.6 g=90% of the theoretical yield.

The product is chromatographed for further purification (silicia gel 0.063–0.2 mm, developing solvent petroleum ether-diether-ether- 1.2).

Yield: 1.7=42.3% of the theoretical yield.

According to this formula, 0.8 g of 4-hydroxybenzyl-benzylcyanide are prepared from 1.0 g of 4-aminobenzylcyanide, corresponding to 50% of the theoretical yield.

2.5. 2-Amino-4-cyanomethyldiphenylmethane

Feedstock:

| 11.5 g = | 32.6 mmole | 4-cyanomethyl-2'-nitrodiphenylmethane, approx. 75% |
| 7.4 g = | 62.3 mmole | tin |
| 33.6 ml = | 342.1 mmole | hydrochloric acid |
| 115.9 ml = | | ethanol |

Procedure:

Into a 500 ml round-bottom multi-neck flask, 11.5 g of 4-cyanomethyl-2'-nitrodiphenylmethane, 7.4 g of tin, and 115.8 ml of ethanol are placed and 33.6 ml of hydrochloric acid is added dropwise within 45 minutes. The mixture is stirred at room temperature for 16 hours. Then the ethanol is siphoned off in a rotary evaporator, and under ice cooling and stirring, the residue is added to 4M of sodium hydroxide solution until a pH of 10 is reached. The undissolved portions are siphoned off via a D-4 frit. The filtrate is extracted three times with 100 ml of diethyl ether each time, and the concentrated organic phases are dried over sodium sulfate. Upon removing the drying agent by filtration, the ether is siphoned off in a rotary evaporator and the residue is chromatographed over silica gel (0.063–03 mm) (developing agent, diethyl ether=petroleum ether—2:1).

Yield: 5.0 g=69.0% of the theoretical yield.

Analogous to this formula, 5.8 g=95.1% of the theoretical yield or 2.4 g=80.0% of the theoretical yield of 4-aminobenzyl-benzylcyanide is prepared from 7.0 g or 3.4 g of 4-nitrobenzyl-benzylcyanide, with 6.1 or 3.0 g of tin, 95.4 ml or 46.3 ml of ethanol and 27.7 ml or 13.5 ml of hydrochloric acid, 32%. The two raw products are combined and chromatographed (silica gel 0.063–0.2 mm, developing agent diethyl ether: petroleum ether—2:1).

Yield: 4.0 g=43.7% of the theoretical yield. $C_{15}H_{14}N_2$ MW 222.29.

2.6 4-Cyanomethyl-2'- or 4'-nitrodiphenylmethane

Feedstock:

| 8.5 g = | 33.8 mmole | 4-chloromethyl-2'-nitrodiphenylmethane |
| 5.1 g = | 32.6 mmole | tetraethyl ammonium cyanide |
| 18.4 ml | | dichloromethane |

Procedure:

In a 100 ml round-bottom flask, 8.5 g of chloromethyl-2'-nitrodiphenylmethane are suspended in 8.4 ml of dichloromethane and the clear solution is added to 5.1 g of tetramethyl ammonium cyanide (dissolved in 10 ml of dichloromethane). The mixture is stirred at room temperature for 20 hours. The the dichloromethane is siphoned off in a rotary evaporator and the residue is suspended in 100 ml of ethyl acetate. The insoluble portions are siphoned off via a D-4 frit, rewashed with ethyl acetate and the filtrate is concentrated in a rotary evaporator.

Yield: 11.5 g.

According to this formula, 7.0 g=66.0% of the theoretical yield of 4-nitrobenzyl-benzycyanide is prepared from 11.0 g=42.0 mmole of 4-chloromethyl-4'-nitrodiphenylmethane, 6.6 g of tetraethyl ammonium cyanide and 36.4 ml of dichloromethane, whereby the residue is suspended in ether, instead of ethyl acetate. The purity of the products obtained corresponds to the nitriles, prepared with sodium cyanide in aqueous ethanol.

$C_{15}H_{12}N_2O_2$ MW 252.235.

2.7 4-Cyanomethyl diphenylmethyl dimethylamine

Feedstock:

| | | |
|---|---|---|
| 15.3 g ≙ | | 53.5 mmole 4-cyanomethyldiphenylmethylbromide |
| 15.3 g = | 17.3 ml ≙ | 136.3 mmole dimethylamine 40% |
| | 85.8 ml | acetone |

In a 250 ml round-bottom flask 15.3 g of a 4-Cyanomethyldiphenyl methylbromide are dissolved in 85.5 ml of acetone and 17.3 ml of dimethyl amine (40%) are added. The clear reaction mixture is stirred for 24 hours at room temperature. The acetone and the excess of dimethyl amine is evaporated off in a rotary evaporator. The residue is dissolved in 100 ml of concentrated hydrochloric acid and the mixture is extracted three times with 50 ml dichlormethane, each to the aqueous phase 4 m aqueous sodium hydroxide is added until pH>11 is reached. Again it is extracted three times with 100 ml of dichloromethane each. The organic extracts are combined and are dried with sodium sulfate. The drying agent is filtered off and the liquid is evaporated on the rotary evaporator. One obtains 6.0 g (44.8% of the theoretical yield) as a crude product which is purified by chromatography on a silicagel column (0.063–0.2 mm) liquid phase; petrol ether-diethyl ether 2:1)

Yield: 3.0 g≙22.4% of the theoretical yield.

2.8 4-Cyanomethyl diphenyl methylmorpholine

In an analogous manner as reported for compound 2.7 15.0 g (52.4 mmole) of 4-cyanomethyl diphenyl methylbromide is reacted with 11.7 ml (133.5 mmole) of morpholine in 84.0 ml of acetone to yield 4-cyanomethyldiphenyl methylmorpholin.

Yield:

2.4 g (15.6% of the theoretical yield) after chromatography on Silicagel, with ether/pentane as eluant).

2.9 4-Cyanomethyl-α-(N-methylpiperazino)-diphenyl methane

In an analogous manner as described for compound 2.7 starting from (70.0 mmole) 4-cyanomethyl diphenyl methylbromide and 19.7 (178 mmole) N-methylpiperazine in 112.0 ml acetone one obtains 4-cyanomethyl-α-(N-methylpiperazino)-diphenylmethan after purification on a silicagel column with methanol.

Yield: 5.5 g≙25.7% of the theoretical yield.

3. PREPARATION OF STARTING COMPOUNDS FOR THE COMPOUND OF FORMULA II

3.1 4-Chloromethylphenyl-4'-fluorophenylmethane

Feedstock:

| | |
|---|---|
| 415.7 mmole p-fluorodiphenylmethane | 77.8 g |
| 415.7 mmole 1,3,5-trioxane | 31.4 g |
| acetic acid 100% | 27.9 ml |

Procedure:

Into a 250 ml round-bottom flask, 8.4 g $ZnCl_2$, 31.4 g of 1,3,5-trioxane, and 77.8 g of p-fluorodiphenylmethane are placed and 27.9 ml of acetic acid are added. The reaction mixture is heated to 60° C. and dried HCl gas is introduced for 3 hours. Following 26 hours of reaction time, the mixture is cooled down to room temperature. 1000 ml of diethyl ether are added to the mixture and the mixture is washed to neutral 16 times with 500 ml $H_2O$, with 500 ml of saturated $NaHCO_3$ solution and 2 times with 500 ml of $H_2O$ each time and dried with sodium sulfate. The drying agent is removed by filtration via a plaited filter and the filtrate is concentrated to the dry state in a rotary evaporator.

Yield: 82.4 g.

The product is isolated by means of vacuum distillation with a Vigreux column (boiling point=111° C./0.15 torr).

Yield: 45.8 g=47.5% of the theoretical yield.

3.2 4-Chloro- or 4-bromophenyl-4'-chloromethylphenylmethane

Feedstock:

| | |
|---|---|
| 6.0 g = | 30.0 mmole p-chlorodiphenylmethane |
| 2.7 g = | 30.0 mmole 1,3,5-trioxane |
| 600.0 mg = | zinc chloride |
| 2.0 mg = | acetic acid, 100% |

In a 50 ml round-bottom multi-necked flask with gas feed tube, condenser, $CaCl_2$ drying tube, and magnetic stirrer, 2.0 ml of acetic acid are added to 6.0 g of p-chlorodiphenylmethane, 1.8 g of 1,3,5-trioxane, 300 mg of zinc chloride, and dry-halogen chloride is introduced for 3 hours at 60° C. Then the mixture is stirred at 60° C. for 18 hours. After this period of time, 0.9 of 1,3,5-trioxane and 300 mg of zinc chloride are one again added to the mixture. After 25 hours reaction time, the solution is cooled to room temperature, added to ice water and extracted with 40 ml of diethyl ether. Then the organic phases are washed 4 times with 20 ml of water each time and 3 times with 20 ml of saturated sodium hydrogen carbonate solution and dried over potassium carbonate. Following removal of the potassium carbonate by filtration, the ether is siphoned off at a rotary evaporator (bath temp. 40° C., water-jet vacuum). The raw product (4.9 g) was distilled in vacuo (oil pump).

Yield: 0.7 g=9.3% of the theoretical yield (b.p. 0.05: 124° C.).

The 4-chlorodiphenylmethane recovered during distillation is added again to the chloromethylation reaction.

The 4-bromo-4'-chloromethyldiphenylmethane is prepared analogously (b.p. 0.05:148° C.).

3.3 4-(4'-Chloromethylbenzyl)benzotrifluoride

Feedstock:

| | | |
|---|---|---|
| 67.7 mmole | 4-trifluoromethyldiphenylmethane | 16.0 g |
| 67.6 mmole | 1,3,5-trioxane | 6.0 g |
| | acetic acid, 100% | |
| | zinc chloride | 1.36 g |

In a 250 ml of round-bottom three-necked flask, 0.68 g of zinc chloride (dried for 3 hours under vacuum at 100° C.); 4.0 g of 1,3,5-trioxane; 16.0 g of 4-trifluoromethyldiphenylmethane and 4.5 ml of 100% acetic acid are combined, heated to 60° C. and dried halogen chloride gas is introduced. The result is a two phase system that turns brown. HCl was introduced for a total of 3 hours. Following 6 hours of reaction time, the conversion is d.c. controlled (developing agent: petroleum benzin 60°-80° C., result: no conversion, starting material). Once again 0.68 g of $ZnCl_2$ and 2.0 g of 1,3,5-trioxane are added to the reaction mixture and stirred overnight. The reaction mixture was stirred for a total of 30 hours at 60° C., whereby following dc result, approximately 20% of the desired compound formed. The mixture was cooled to room temperature and diluted with 150 ml of diethyl ether. The ether solution was washed to neutral several times with a total of 2.5 liters of water. The organic phase was shaken once with 80 ml of a saturated sodium hydrogen carbonate solution and then washed to neutral 2 times with 90 ml of water each time. The organic phase was dried over sodium sulfate. The drying agent was removed by filtration and the filtrate was concentrated in a rotary evaporator (30° C., water-jet vacuum).

The raw product was purified by means of fractional distillation. In order to separate the nonconverted 4-trifluoromethyldiphenylmethane, the mixture was distilled via a Vigreux column. Then the 4-(4'-chloromethylbenzyl)benzotrifluoride was distilled over without a column.

4-Trifluoromethyldiphenylmethane: boiling range: 58°-63° C. at 0.1-0.2 torr.

4-(4'-Chloromethylbenzyl)benzotrifluoride: boiling range 80°-83° C. at 0.1 torr.

Yield: 7.0 g (=20.0% of the theoretical yield, calculated for added starting material of the feedstock concentrated for distillation!).

3.4 4-Cyanomethyl diphenyl methylbromide

Feedstock:

| | |
|---|---|
| 11.4 g = | 54.7 mmole 4-cyanomethyldiphenylmethane |
| 9.9 g = | 54.7 mmole N—bromsuccinimide |
| 55.9 ml | carbon tetrachloride, abs. |
| 114 mg | dibenzoylperoxide |

In a 250 ml round bottom three neck flask equipped with condenser, drying tube with gas exit tube and magnetic stirrer 11.4 g of 4-cyanomethyl-diphenyl methane are dissolved in 55 ml of carbon tetrachloride and 9.9 g of N-bromo succinimide are added. To the suspension 114 mg of dibenzoyl peroxide are added and the mixture is refluxed for one hour. The red colour of the mixture which appears when boiling starts will fade to a large extent toward the end of the reaction period. After cooling the suspension to room temperature the succinimide which is formed is filtered off and is washed with diethyl ether. The combined filtrates are evaporated on a rotary evaporator.

Yield: 15.3 g.

The product should be used without further purification for reacting since it decomposes on distillation (0.5 Torr) as well as on chromatography on silica gel (ether/pentane). Moreover no suitable solvent for recrystallization was found.

4. PREPARATION OF COMPOUNDS OF FORMULA VI

4.1 4-Bromomethylbenzophenone

Feedstock:

| | | |
|---|---|---|
| 9.8 g = | 49.9 mmole | p-methylbenzophenone |
| 2.6 ml = | 102.2 mmole | bromine, reagent grade |

Procedure:

A 9.8 g amount of 4-methylbenzohenone was heated to 150° C. and bromine was slowly added dropwise to the melt. Then the feedstock was stirred at 150° C. for one hour. Following cooling to room temperature, the mixture was poured into water and extracted with 100 ml of dichloromethane.

The organic phase was dried over sodium sulfate; and following removal of drying agent by filtration, concentrated in a rotary evaporator. Residue (12.4 g-90.3% of the theoretical yield) was recrystallized from 120 ml of 90% ethanol, using 1.2 g of activated carbon.

Yield: 7.2 g (=52.4% of the theoretical yield).

The compounds of formula I and the acidic addition salts derived from them with the physiologically compatible acids are quite suitable for intravenous application.

The pharmacological action can be demonstrated with the following compounds of formula I as examples:

Compound 1.1: 2,4,7-Triamino-6[4(4'-fluorobenzyl)-phenyl]-pteridine (=p-fluorobenzyl-triamterene)

Compound 1:2: 2,4,7-Triamino-6[4(4'-chlorobenzyl)-phenyl]-pteridine (=p-chlorobenzyl-triamterene)

Compound 1:3: 2,4,7-Triamino-6[4(4'-bromobenzyl)-phenyl]-pteridine

Compound 1:4: 2,4,7-Triamino-6[4(4'-trifluorobenzyl)-phenyl]pteridine

Compound 1:5: 2,4,7-Triamino-6[4(4'-hydroxybenzyl)-phenyl]pteridine (=hydroxybenzyl-triamterene)

Compound 1:6: 2,4,7-Triamino-6[4(4'-hydroxybenzyl)-phenyl]pteridine (=p-hydroxybenzyl-triamterene)

Compound 1:7: 2,4,7-Triamino-6-[4-(α-hydroxybenzyl)phenyl]pteridine (=p(α-hydroxybenzyl-triamterene)

Reference substances:

Compound TA: Triamterene

Compound BzTA: 2,4,7-Triamino-6-[4(4'-benzyl)-phenyl]-pteridine (=benzyl triamterene)

The diuresis tests were conducted according to the following method:

Diuresis tests/Method:

Male Wistar rats, weighing approximately 130 g, were used for the tests; food had been withdrawn from them for 18 hours. Immediately before the intravenous administration of the test substance, they were orally fed a quantity of 20 ml/kg 0.9% NaCl solution. The intravenous application ranged from 0.001 to 300 μmol of active substance in 4 ml/kg of 9% NaCl solution (pH 3). Under a slight anesthesia, administration was in the caudal vein. Generally six experimental animals were used per test. The peroral administration was by means of probang in the gastrointestinal region. The animals were individually placed into diuresis cages and the urine collected after 2.5 hours. The electrolytes (Na+/K+,Mg+2) were determined by means of flame photometry and by means of atom absorption measurement with the FL 6 electrolyte automatic equipment from Zeiss in Oberkochen.

Curves for dose/response correlations were obtained with the aid of non-linear regression analysis by means of thekochen.

Curves for dose/response correlations were obtained with the aid of non-linear regression analysis by means of thekochen.

Curves for dose/response correlations were obtained with the aid of non-linear regression analysis by means of the NONLIN computer program by C. Daniel and F. S. Wood in "Fitting Equations to Data," J. Wiley & Sons, New York, 1980.

(a) Volume of urine following administration of 10 μmol/kg of active substance of formula I as described above:

| active substance | intraveneous (i.v.) volume of urine (ml/kg) | oral (p.o.) volume of urine (ml/kg) |
|---|---|---|
| 1.1 | 20.25 | 18.32 |
| 1.3 | 16.16 | |
| 1.4 | 12.88 | 11.42 |
| 1.5 | 19.56 | 12.35 |
| 1.6 | 15.03 | 14.63 |
| TA | 16.13 | 20.88 |
| BzTA | 20.16 | 21.18 |
| control | 5.06* | 7.56** |

*control with 0.5% (R) Tylose solution
**control with 20% polyethylene glycol

| active substance | intraveneous (i.v.) volume of urine (ml/kg) | oral (p.o.)* volume of urine (ml/kg) |
|---|---|---|
| 1.2 | 17.80 | 18.61 |
| TA | 18.3 | 23.4 |
| BzTA | 18.8 | 15.7 |
| control | 8.1 | 3.95 |

*with 5 animals

| active substance | intraveneous (i.v.)* volume of urine (ml/kg) | oral (p.o.)* volume of urine (ml/kg) |
|---|---|---|
| 1.7 | 21.9 | 17.4 |
| TA | 15.8 | 10.9 |
| BzTA | 21.4 | 22.0 |
| control | 8.4 | 5.45 |

*with 5 animals

Result:
All active substances of formula I show increased excretion of urine with respect to the control and in part with respect to the reference substances.

(b) elimination of sodium/elimination or potassium following administration of 10 μmol intraveneous/peroral (analysis as described)

| active substance | intraveneous Na (mmol/kg) | peroral Na (mmol/kg) | intervenous K (mmol/kg) | peroral K (mmol/kg) |
|---|---|---|---|---|
| 1.1 | 2.71 | 2.28 | 0.47 | 0.19 |
| 1.3 | 1.45 | | 0.66 | |
| 1.4 | 1.03 | 1.14 | 0.44 | 0.43 |
| 1.5 | 2.80 | 0.76 | 0.32 | 0.487 |
| 1.6 | 1.63 | 1.14 | 0.434 | 0.397 |
| TA | 1.77 | 2.24 | 0.56 | 0.45 |
| BzTA | 3.14 | 3.04 | 0.26 | 0.16 |
| control | 0.36 | 0.51 | 0.51 | 0.41 |

| active substance | intraveneous Na (mmol/kg) | peroral Na (mmol/kg) | intervenous K (mmol/kg) | peroral* K (mmol/kg) |
|---|---|---|---|---|
| 1.2 | 1.99 | 1.91 | 0.069 | 0.27 |
| TA | 1.54 | 2.82 | 0.12 | 0.26 |
| BzTA | 2.05 | 2.15 | 0.06 | 0.08 |
| control | 0.83 | 0.86 | 0.28 | 0.32 |

| active substance | intraveneous* Na (mmol/kg) | peroral* Na (mmol/kg) | interveneous* K (mmol/kg) | peroral* K (mmol/kg) |
|---|---|---|---|---|
| 1.7 | 2.69 | 3.20 | 0.08 | 0.10 |
| 1.8 | 4.79 | 4.97 | 0.20 | 0.20** |
| 1.9 | 4.14 | 2.61 | 0.34 | 0.31 |
| 1.10 | 3.63 | 2.86 | 0.15 | 0.41 |
| TA | 2.12 | 1.46 | 0.39 | 0.11 |
| BzTA | 2.77 | 3.35 | 0.24 | 0.16 |
| control | 0.71 | 0.35 | 0.49 | 0.19 |

*with 5 animals
**with 4 animals

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A pharmaceutically efficacious pteridine compound of formula:

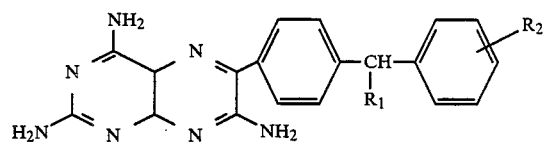

wherein $R_1$ is hydrogen, halogen, trifluoromethyl, nitro, a —$(A)_n$—$OR_3$ group, wherein $R_3$ is hydrogen or a $C_{1-6}$ alkyl group, a —$(A)_n$—$NR_4R_5$ group, wherein $R_4$ and $R_5$ independently of each other are hydrogen or a $C_{1-6}$ alkyl group or $R_4$ and $R_5$ together with the nitrogen atom form a 5- or 6-membered ring that is substituted with a $C_{1-4}$ alkyl group and wherein A is a linking group having 1 to 6 linking carbon atoms, one of which can be replaced by oxygen and wherein n is zero or one, and wherein $R_2$ is hydrogen or, independently of $R_1$, has the same meaning as $R_1$, with the proviso that $R_1$ and $R_2$ are not simultaneously hydrogen, and the physiologically acceptable acid addition salts thereof.

2. The pharmaceutically efficacious pteridine compound of claim 1, wherein the salt is a hydrochloride, hydrobromide, sulfate, citrate, tartrate, succinate, maleinate, fumarate, lactate or benzoate.

3. The pteridine compound of claim 1, which is 2,4,7-triamino-6-[4-(4'-chlorobenzyl)-phenyl]-pteridine, 2,4,7-triamino-6-[4-(4'-fluorobenzyl)-phenyl]-pteridine, 2,4,7-triamino-6-[4-(4'-bromobenzyl)-phenyl]-pteridine, 2,4,7-triamino-6-[4-(4'-trifluoromethylbenzyl)-phenyl]-pteridine, 2,4,7-triamino-6-[4-(4'-hydroxybenzyl)-phenyl]-pteridine, 2,4,7-triamino-6-[4-(4'-nitrobenzyl)-phenyl]-pteridine, 2,4,7-triamino-6-[4-(4'-aminobenzyl)-phenyl]-pteridine,. 2,4,7-triamino-6-[4-(α-N-dimethyl-aminobenzyl)-phenyl]-pteridine 2,4,7-triamino-6-[4-(α-morpholinobenzyl)-phenyl]-pteridine or 2,4,7-triamino-6-[4-(α-N,N-methylpiperazino)benzyl)-phenyl]-pteridine.

4. A cardioactive efficacious preparations, comprising:
   a therapeutically effective amount of at least one pteridine compound of formula I in claim 1 in combination with a pharmaceutically acceptable excipient.

5. The cardioactive efficacious preparation of claim 1, wherein the quantity of active pteridine compound of formula I is such that it provides from 1 to 100 mg per unit dose.

6. A method of treating cardiac arrhythmia, comprising:
   administering a therapeutically effective amount of the compound of claim 1 to a host subject.

7. The method of claim 6, wherein from 1 to 100 mg of said pteridine compound is administered per kg of body weight.

* * * * *

UNITED STATES PATENT AND TRADEMARK OFFICE
CERTIFICATE OF CORRECTION

PATENT NO. : 4,874,763

DATED : OCTOBER 17, 1989

INVENTOR(S) : Ingrid HOFMANN et al

It is certified that error appears in the above-identified patent and that said Letters Patent is hereby corrected as shown below:

Cover page, in the Abstract: change " 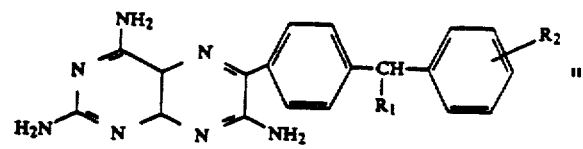 "

to

-- 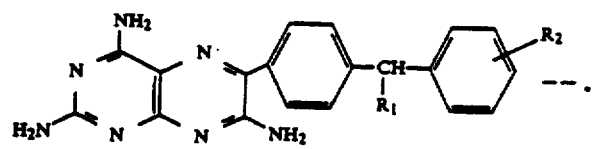 --.

Column 2, line 27: change " 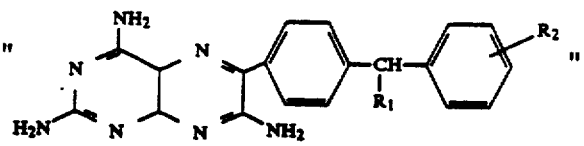 "

to -- 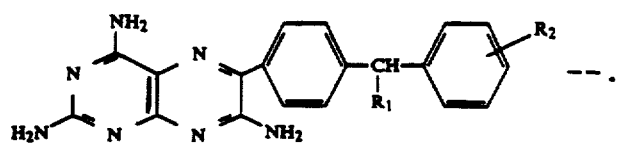 --.

UNITED STATES PATENT AND TRADEMARK OFFICE
CERTIFICATE OF CORRECTION

PATENT NO. : 4,874,763
DATED : OCTOBER 17, 1989
INVENTOR(S) : Ingrid HOFMANN et al It is certified that error appears in the above-identified patent and that said Letters Patent is hereby corrected as shown below:

Column 3, line 36: change "[p-($\alpha$-hydroxyenzyl)-" to -- [p-($\alpha$-hydroxybenzyl)- --.

Column 4, line 44: change "acid" to -- aid --.

Column 8, line 18: change "membrance" to -- membrane --.

Column 13, line 39: change "60°-80°C0-diethyl" to -- 60°-80°C.:diethyl --.

Column 14, line 21: delete "=";
line 68: change "The" to -- Then --.

Column 15, line 8: change "4-nitrobenzyl-benzycyanide" to -- 4-nitrobenzyl-benzylcyanide --;

line 64: after "19.7", insert -- ml --.

Column 16, line 11: change the solid line to

-- zinc chloride (3 hours, $10^{-1}$ torr/100°C)   8.4 g $ZnCl_2$ --;

UNITED STATES PATENT AND TRADEMARK OFFICE
CERTIFICATE OF CORRECTION

PATENT NO. : 4,874,763
DATED : OCTOBER 17, 1989
INVENTOR(S) : Ingrid HOFMANN et al It is certified that error appears in the above-identified patent and that said Letters Patent is hereby corrected as shown below:

Column 16, line 12: insert the solid line originally in line 11;

line 40: change "600.0 mg =" to -- 600 mg --;
    line 41: delete "=";
    line 49: after "0.9", insert -- g --;
    line 50: change "one" to -- once --.

Column 18, line 21: change "4-methylbenzohenone" to -- 4-methylbenzophenone --.

Column 19, lines 10-15: delete in their entirety.

UNITED STATES PATENT AND TRADEMARK OFFICE
CERTIFICATE OF CORRECTION

PATENT NO. : 4,874,763      Page 4 of 4
DATED : OCTOBER 17, 1989
INVENTOR(S) : Ingrid HOFMANN et al It is certified that error appears in the above-identified patent and that said Letters Patent is hereby corrected as shown below:

Column 20, line 33: change

" 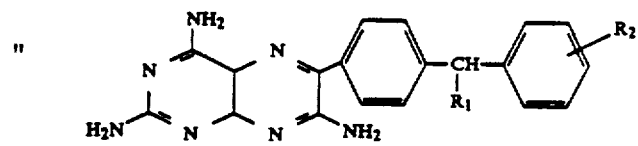 "

to

-- 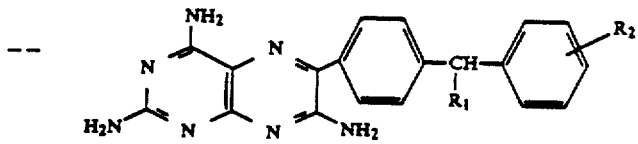 --.

Signed and Sealed this

Twenty-eighth Day of April, 1992

*Attest:*

HARRY F. MANBECK, JR.

*Attesting Officer*      *Commissioner of Patents and Trademarks*